United States Patent [19]

Solomon et al.

[11] Patent Number: 5,122,330

[45] Date of Patent: Jun. 16, 1992

[54] SENSOR FOR MONITORING CORROSION ON A MEMBER IN A NUCLEAR REACTOR CORE

[75] Inventors: Harvey D. Solomon, Schenectady, N.Y.; Gerald M. Gordon, Soquel, Calif.

[73] Assignee: General Electric Company, Schenectady, N.Y.

[21] Appl. No.: 624,828

[22] Filed: Dec. 10, 1990

[51] Int. Cl.$^5$ .............................................. G21C 17/00
[52] U.S. Cl. .................................. 376/245; 376/305; 324/700
[58] Field of Search ............... 376/245, 246, 247, 258, 376/305; 324/699, 700

[56] References Cited

U.S. PATENT DOCUMENTS

| | | | |
|---|---|---|---|
| 3,042,863 | 7/1962 | Marsh et al. | 324/71 |
| 3,197,724 | 7/1965 | Marsh | 338/13 |
| 3,358,229 | 12/1967 | Collins | 324/65 |
| 3,599,090 | 8/1971 | Fitzpatrick et al. | 324/71 C |
| 3,604,102 | 9/1971 | Boccalari et al. | 29/474.3 |
| 3,854,087 | 12/1974 | Frenck et al. | 324/65 CR |
| 3,913,208 | 10/1975 | Colombi et al. | 29/417 |
| 4,338,563 | 7/1982 | Rhoades et al. | 324/65 CR |
| 4,677,855 | 7/1987 | Coffin, Jr. et al. | 73/799 |
| 4,924,708 | 5/1990 | Solomon et al. | 73/799 |

OTHER PUBLICATIONS

Urquhart, A. W. and D. A. Vermilyea, "A Preliminary Correlation Between the Accelerated Corrosion of Zircaloy in BWR's and in High Temperature, High Pressure Steam" *Journal of Nuclear Materials*, Jun., 1976, pp. 111-114.

*Primary Examiner*—Brooks H. Hunt
*Assistant Examiner*—Chrisman D. Carroll
*Attorney, Agent, or Firm*—James E. McGinness; James C. Davis, Jr.; James Magee, Jr.

[57] ABSTRACT

An apparatus and method for monitoring corrosion to members within the core of a nuclear reactor, particularly fuel rod cladding. A sensor means is submerged inside the core of a nuclear reactor near the member of fuel rods. The sensor means is comprised of a generally cylindrical section having an outer surface that is subject to corrosion and radiation, and has a cross-sectional area $A_1$. The sensor means additionally has a reference section subjected to radiation but not to corrosion, and having a cross-sectional area $A_2$. At least one pair of first probes, separated by a length $L_1$, is placed in electrical contact with the cylindrical section. At least one pair of second probes separated by a length $L_2$, is placed in electrical contact with the reference section. A current is passed throughout the sensor means to produce a potential gradient in the cylindrical section and reference section. The change in potential in the reference section, and the cylindrical section is measured and used to calculate the subsequent cross-sectional area in the cylindrical section between the first probes. Preferably, the cylindrical section and reference section are made from the same material as the member.

10 Claims, 1 Drawing Sheet

SENSOR FOR MONITORING CORROSION ON A MEMBER IN A NUCLEAR REACTOR CORE

This invention relates to an apparatus and method for monitoring corrosion to members in the core of a nuclear reactor. This invention further relates to an apparatus and method for detecting general and nodular corrosion occurring to nuclear reactor fuel cladding, i.e., the material used to contain the fuel in a shape such as a rod or plate-like shape.

BACKGROUND OF THE INVENTION

Nuclear reactors are used today in numerous ways, e.g., to generate electric power and for special tests. Nuclear power plants employ a nuclear reactor. The fuel is a radioactive material which undergoes a fission reaction. Nuclear fission is the splitting of the atomic nucleus, usually into two or three larger particles, two or more neutrons, and other smaller particles with the release of a relatively large amount of energy. The average amount of energy released in the various fission reactions is about 200 $M_eV$ (million electron volts), which is dramatically higher than the energy produced from a chemical reaction such as oxidation which is used in fossil-fuel plants when coal or oil is burned.

During nuclear fission in energy production, an exceedingly large amount of energy is released and excess neutrons are produced which permits a chain reaction. These factors make it possible to design nuclear reactors which are self-sustaining, i.e., wherein reactions occur with the continuous release of energy.

Some current light-water cooled nuclear power plants utilize uranium oxide as a fuel. Solid cylindrical rods, instead of plates, are the most common shape for the fuel. For most reactor applications, these fuel rods are protected by a cladding of aluminum, stainless steel, zirconium or zirconium alloy and are assembled into a unit. Other typical constituents of reactors include aluminum-clad uranium metal for plutonium production reactors, stainless steel-clad $UO_2$ dispersed in stainless steel for propulsion reactors, and zirconium or stainless steel-clad $UO_2$ pellets for central station power reactors.

Zirconium is used in nuclear technology because of its properties which include insolubility in water and cold acids, corrosion resistance, low neutron absorption, and low toxicity. In addition to these desirable properties, zirconium also exhibits good strengths at high temperatures, corrosion resistance to high velocity coolants, avoidance of formation of highly radioactive isotopes, and resistance to mechanical damage from neutron radiation. An important application for zirconium is as the base metal in an alloy known as Zircaloy II, comprised of 1.5% tin, 0.35% iron-chromium-nickel, 0.15% oxygen, and the balance zirconium. This alloy is widely used in water cooled nuclear reactors because of its excellent corrosion resistance up to about 350 degrees in $H_2O$, and its low neutron cross-section. The term "Zircaloy" is a trademark for alloys of zirconium and nickel which are used as cladding for nuclear fuel elements and for other reactor applications. "Zircaloy II" is a particular Zircaloy.

Even though corrosion-resistant alloys are used to clad the fuel, radiation damage and corrosion can still occur to these alloys. Corrosion is usually the destruction, degradation or deterioration of material due to the reaction between the material and its environment. In a restricted sense corrosion consists of the slow chemical and electrochemical reactions between a metal and its environment; in a broader sense corrosion is the slow destruction of materials by chemical agents and electrochemical reactions.

The severe environment in the core of a boiling water nuclear reactor can include temperatures of 290° C. or greater, pressures of 1,000 psi or greater, and radiation of $10^9$ rads per hour gamma and $10^{13}$ rads per hour neutron. The Zircaloy alloys are among the best corrosion resistant materials when tested in water at reactor operating temperatures, about 290° C., but without exposure to nuclear radiation. The corrosion rate under these conditions is very low and the corrosion product is a uniform, tightly adherent, black $ZrO_2$ film. In actual service, however, the Zircaloy is irradiated and is also exposed to radiolysis products present in reactor water. The corrosion resistance properties of Zircaloy deteriorate under these conditions and the corrosion rate thereof is accelerated.

The deterioration under actual reactor conditions of the corrosion resistance properties of Zircaloy is not manifested in merely an increased uniform rate of corrosion. Rather, in addition to the black $ZrO_2$ layer formed, a localized, or nodular corrosion phenomenon has been observed especially in boiling water reactors. In addition to producing an accelerated rate of corrosion, the corrosion product of the nodular corrosion reaction is a highly undesirable white $ZrO_2$ bloom which is less adherent and lower in density than the uniform corrosion product of black $ZrO_2$.

The increased rate of corrosion caused by the nodular corrosion reaction will be likely to shorten the service life of the tube cladding, and also this nodular corrosion will have a detrimental effect on the efficient operation of the reactor. The white $ZrO_2$, being less adherent, may be prone to spalling or flaking away from the tube into the reactor water. On the other hand, if the nodular corrosion product does not spall away, a decrease in heat transfer efficiency through the tube into the water is created when the nodular corrosion proliferates and the less dense white $ZrO_2$ covers all or a large portion of a tube.

It is, therefore, desirable to be able to detect or monitor the corrosion, e.g., nodular corrosion or general corrosion, to the fuel cladding and other members in a reactor core.

It is, therefore, an object of this invention to provide an apparatus and method of monitoring corrosion to members such as nuclear fuel cladding in the core of a nuclear reactor. It is another object of this invention to provide such an apparatus and method for monitoring of corrosion to such members by measuring potential changes in a sensor located in the nuclear reactor core. Furthermore, it is an object of this invention to monitor corrosion on a scored surface area on the sensor, e.g., to monitor nodular corrosion that is promoted by such scoring. It is also an object of this invention to provide such an apparatus and a method employing the apparatus wherein the sensor is comprised preferably of zirconium, and even more preferably of a zirconium alloy or "Zircaloy" alloy. It is even further preferred that the zirconium, zirconium alloy or Zircaloy alloy be from the same lot as that used to form, for example, the fuel cladding.

SUMMARY OF THE INVENTION

The method and apparatus of this invention provides means for monitoring corrosion to members in the core of a nuclear reactor, by measuring electrical potential changes in a sensor located in the reactor core. Nuclear radiation causes increased atom motion and metallurgical changes such as formation of vacancies, precipitates, or recrystallization that causes increased resistivity in the sensor, and accounts for some of the potential change in the sensor. Therefore, the potential change from radiation induced changes in resistivity is separately measured in the sensor and factored out to give the potential change resulting from loss of cross-section due to corrosion of the sensor. The corrosion measured includes general corrosion and, in particular, nodular corrosion of fuel cladding.

In the method of the invention, corrosion on a member in a nuclear reactor core is estimated by placing a sensor means in close proximity to the member, and in contact with the coolant water circulating in the reactor core. The sensor means is comprised of a generally cylindrical section having an outer surface that is subject to corrosion and radiation, and has a cross-sectional area, $A_1$. The sensor means additionally has a reference section subjected to radiation but not to corrosion, and having a cross-sectional area, $A_2$. At least one pair of first probes, separated by a length, $L_1$, is placed in electrical contact with the cylindrical section. At least one pair of second probes separated by a length, $L_2$, is placed in electrical contact with the reference section. A current is passed throughout the sensor means to produce a potential gradient in the cylindrical section and reference section. The change in potential in the reference section, and the cylindrical section is measured and used to calculate the subsequent cross-sectional area, $A_i$, in the cylindrical section between the first probes. Preferably, the cylindrical section and reference section are made from the same material as the member. Most preferably, the cylindrical section and reference section also have the same crystalline texture as the member.

The apparatus of this invention has a sensor means comprised of a generally cylindrical section and a reference section. The cylindrical section has sidewall means extending from a base to define an annular channel therein. An inner surface of the cylindrical section faces the annular channel and an oppositely facing outer surface is subjected to the core environment. Preferably, the outer surface has a scored area for promoting nodular corrosion, and a smooth area. The reference section is positioned within and attached to the base so that a current can be passed throughout the sensor means, the sensor means being sealed so that the reference section is not exposed to the water in the nuclear reactor core. The sensor means is preferably comprised of the same material as the member on which corrosion is being estimated, for example, for fuel cladding members zirconium, zirconium alloy, or Zircaloy, or more preferably Zircaloy II, and most preferably the same lot of material as that used to form the cladding is used to form the sensor means. Both the cylindrical section and reference section have current leads and potential probes connected thereto, from within the apparatus.

A constant electric current, preferably a direct current having a periodically reversed polarity, is passed throughout the cylindrical section and reference section by way of the leads in electrical connection therewith from within the apparatus. The potential probes are used to measure the potential of the current passing through the cylindrical section and reference section. The potential measured in the cylindrical section corresponds to the subsequent cross-section, or remaining wall thickness of the cylindrical section due to corrosion of the outer surface, and to radiation induced changes in resistivity. By factoring out the potential change due to radiation, as measured in the reference section, the potential change from corrosion alone can be determined in the cylindrical section, and the change in cross-section, or thickness, of the cylindrical section due to corrosion can be calculated from the potential measurements.

A more particular embodiment of the apparatus of this invention provides an apparatus for monitoring corrosion of nuclear reactor fuel cladding, comprising: a generally cylindrical sensor member comprised of sidewall means extending from a first end to a second end, the sidewall means extending to a first access opening at the first end and to a second access opening at the second end, the sidewall means having an outer surface, an interior, and a first annular channel extending in the interior from the first end to the second end, and, the outer surface having at least one scored region; a first generally circular end cap means sealably positioned over or attached to the first access opening in relationship therewith so that the first cap retains the first annular channel substantially moisture-free; an elongated rod located inside the first annular channel and attached to the first end cap; a generally cylindrical sleeve means formed of a select metal and comprises of sleeve sidewall means extending from a first sleeve end to a second sleeve end, the sleeve sidewall means extending to a first sleeve access opening at the first sleeve end, to a second sleeve access opening at the second sleeve end, and, the sleeve sidewall means having an interior and a second annular channel extending in the interior from the first sleeve end to the second sleeve end; a generally cylindrical transition member of a select member compatible with both of the sensor member and the sleeve, the transition member comprised of transition sidewall means extending from a first transition end to a second transition end, the transition side wall means extending to a first transition access opening at the first transition end, to a second transition access opening at the second transition end, and, the transition sidewall means having an interior and a third annular channel extending in the interior from the first transition end to the second transition end; the transition member at the first transition end being sealably connected to the second end of the sensor member and the transition member at the second transition end being sealably connected to the first sleeve end of the sleeve means so that the first, second and third annular channels are generally concentric and contiguous, and so that the first, second and third annular channels are retained substantially moisture-free; a first lead in electrical contact with the interior of the sensor member, and a second lead in electrical contact with the rod, the first and second leads insulatively extending from the interior of the sensor member and rod through the first, second and third channels; at least two pairs of probes, a first pair in electrical contact with the interior of the sensor member, and a second pair in electrical contact with the rod for detecting electrical potential, the probes insulatively extending from the interior of the sensor member and rod through the first, second and third channels; and, a second end cap sealably attached to the second sleeve end of the sleeve so that the first, second and third channels are retained substantially moisture free, the second end cap means further comprising means defining at least one opening through which the probes and the first and second leads pass in a moisture-proof seal.

Other objects of the invention will, in part, be obvious and will, in part appear hereinafter.

The invention, accordingly, comprises the apparatus possessing the construction, combination of elements, and arrangements of parts which are exemplified in the following detailed disclosure; and, method employing the same. For a fuller understanding of the nature and objects of the invention, reference should be made to the following detailed description taken in connection with the accompanying drawings.

DETAILED DESCRIPTION OF THE INVENTION

Figure 1:
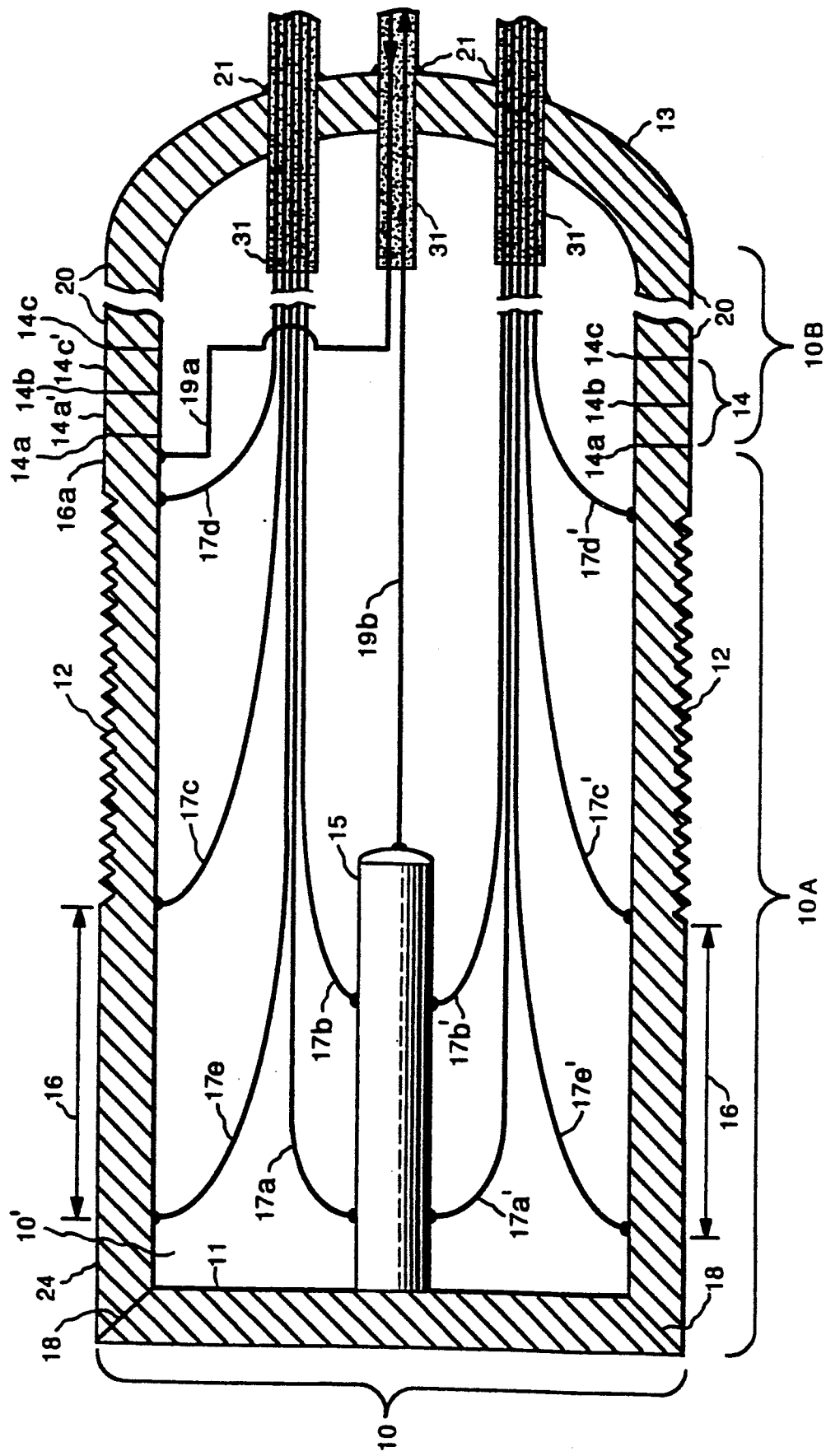
FIG. 1 shows a partial sectional view of a sensor according to the present invention.

While having utility in a broad variety of industrial monitoring functions, the apparatus of the present invention finds particular use operating under the hostile environment of a nuclear reactor core. The assembly of the present invention generally comprises brazed and welded metal parts, which are corrosion-resistant.

The apparatus preferably has two zones on the outer sensing surface. One zone comprises a scored section, i.e., a section which is threaded, striated, grooved, roughened, scratched, or otherwise altered to increase surface area, preferably scored to a one mil deep fine pitch spiral, to promote the formation of nodular corrosion. The second zone is a substantially smooth surface wherein the average change in potential and accordingly corrosion on the outer sensing surface is determine. The first zone has corrosion, and in particular nodular corrosion, occurring at a faster rate because of the scored surface. The reference section, not being exposed to the core water, undergoes a change in potential due to radiation damage, and, should not have corrosion occurring on it.

It is preferred that potential in the sensor means be measured at three points, i.e., at the first and second zones on the outer sensing surface, and at the reference section. From these three measurements, the accelerated nodular, and more general corrosion occurring on the cylindrical section is determined. From these potential measurements the change in cross-section due to corrosion of the fuel cladding can be determined because the sensor means of the apparatus of this invention, preferably is fabricated out of the same material as the cladding; or, out of a material which undergoes corrosion and radiation damage in the same manner as the cladding. So that the corrosion and damage to the sensor reflects the corrosion and damage occurring to the fuel cladding, it is most preferred that the sensor means be fabricated from the same lot of material used for making the fuel cladding. In this way, the same crystalline texture found in the fuel cladding that is, for example, formed by pilger rolling tube reduction and beta quenching can be present in the cylindrical section and reference section of the sensor means. So that the potential measurements from the sensor means correspond as accurately as possible to the corrosion occurring on the fuel cladding, it is also preferred that the apparatus to be set in place in the reactor when the fuel is installed. Further, the thickness or cross-section of the cylindrical section is preferably about the same as that of the fuel cladding.

Note, however, one need only have one zone on the cylindrical section, e.g., the substantially smooth zone and take only potential measurement relative to that, e.g., only two potential probes attached to the inside. The sensor, when used is preferably placed in the core of a nuclear reactor, as near as possible to the nuclear fuel rods or other member on which corrosion is being simulated. The apparatus can be any suitable size, including the size of a fuel rod. The cylindrical section is sealed so that the reference section is not exposed to corrosion from the reactor core coolant water. This sealed-tight environment ensures that the potential change in the reference section is not due to corrosion. Accordingly, the circular base from which the sidewall means extend is sealed thereto, and the circular base is made of the same material as the cylindrical section and the reference section. The potential change of the reference section which is due to radiation damage alone enables on e to determine potential change in the cylindrical section from this effect. Further, the reference section potential change coupled with a knowledge of the core water temperature enables one to correct for potential change due to water temperature.

Further more, the sensor is preferably attached to a sleeve. The sleeve is preferably stainless steel. Because stainless steel cannot be welded to zirconium or Zircaloy alloys, the attachment is preferably a transition piece; and, when the sensor is a Zircaloy alloy, the attachment is a stainless steel to zircaloy joint or transition piece, which will insulate the wires for the leads and potential probes within the apparatus from the nuclear reactor coolant water. The attachment is more preferably by a bonded Zircaloy II to stainless steel transition piece. A preferred embodiment of the transition piece calls for a Zircaloy to Zircaloy connection and stainless steel to stainless steel connection. This transition piece is fabricated by any suitable means, including by co-extruding a Zircaloy alloy tube with a stainless steel tube to form a metallurgical bond between the tubes. A section of the inner tube is removed from one end of the transition piece, and a section of the outer tube is removed from the other end, and the Zircaloy end is welded to the cylindrical section and the stainless steel end is welded to the sleeve. The attachment can also be made by brazing the cylindrical section to the sleeve, or brazing a section of a compatible material such as Kovar alloy therebetween. Kovar alloys are comprises of by weight percent, about 53.8% Fe, 29% Ni, 17% Co, and 0.2% Mn.

Mineral insulated stainless steel, nickel, or preferably platinum wires can be employed for the probe and lead wires. The wires are preferably fastened, e.g., welded, to suitable places on the inner surfaces of the sensor. The mineral insulated wires have a metal jacket of, for example, stainless steel on the portion of the wire at least outside of the sensor. If the metal jacket on the wires was made from zirconium alloy, Zircaloy alloy, or Zircaloy II alloy, the sleeve could be formed from the same zirconium alloy and the attachment to the sensor means could be by brazing or welding without a separate transition member. This is because the zirconium alloy wire jacket can be brazed to form a moisture-proof seal with the opening in the end cap of the sleeve.

In the embodiment of the invention shown in FIG. 1, the sensor means of the apparatus has a substantially hollow cylindrical section, having a cross-section $A_1$, with a scored section and a substantially smooth surface section on the outer surface. The sensor means also includes an elongated rod, having a cross-section $A_2$, within the interior of the cylindrical section. The sensor means is connected to a transition piece which is welded or brazed onto the structure. The transition piece is also connected to a sleeve. The sensor means undergoes changes in potential and by monitoring those changes, corrosion on the exterior of the sensor can be determined. The corrosion occurring on the sensor reflects the corrosion on the fuel cladding.

Referring to FIG. 1, the structure of the apparatus according to the present invention is represented in general at 10 in sectional fashion. Apparatus 10 has a generally cylindrical shape and is divided into sensor portion 10A and sleeve portion 10B; the latter including transition member 14 and sleeve 20. Apparatus 10 is further comprises of components including: first end cap 11, second end cap 13, a cylindrical section 24 having a smooth sensor section 16 and a scored section 12; potential probes 71a–e, and 17a'–e'; leads 19a and 19b; and inner rod 15 attached to first end cap 11. Preferably, rod 15 and end cap 11 are formed as a single piece. Most preferably, rod 15 is a piece of fuel rod cladding having the same composition and crystal texture as the fuel rod cladding on which corrosion is being monitored. Weld 18 is used to seal first end cap 11 to cylindrical section 24. End cap 11 is preferably of the same material as sensor portion 10A and rod 15, preferably Zircaloy II.

An electric current enters through lead 19a and can exit through the rod 15 by way of lead 19b. When the current passes through the scored section 12, potential probes 17c and 17d or 17c' and 17d' attached to scored section 12 can monitor any change in potential occurring in this section. Probes 17c and 17e, or 17c' and 17e' can be used to measure any change in potential in smooth sensor section 16 (i.e., the area of sensor portion 10A between probes 17c and 17e, or 17c' and 17e'). Further, probes 17a and 17b, or 17a' and 17b' can be used to measure any change in potential in rod 15. While ten probes (17a–e, and 17a'–e') are shown in FIG. 1, apparatus according to this invention can have as few as four (4) probes, two probes in electrical contact with rod 15 and two probes in electrical contact with, for example, smooth section 16. Likewise, the leads can be placed in any suitable location. Inner rod 15 is also preferably comprised of a Zircaloy alloy. It is preferred that rod 15 exist in a moisture-free environment within apparatus 10, i.e., that rod 15 not be exposed to the coolant water in the reactor core. Thus, rod 15 is situated within apparatus 10. Weld 18 seals end cap 11 pressure tight.

Probes 17a–e and 17a'–e'are spot welded to the inner surface of apparatus 10 to prevent corrosion and loss of electrical contact between the probes and the apparatus. The probes can be formed from stainless steel, platinum, nickel, or any other metal or alloy or conductor having suitable properties. The probe wires are covered with a mineral insulator (not shown), e.g., ceramic material comprised of such compounds as magnesium oxide (MgO) or aluminide oxide ($Al_2O_3$). Suitable properties for the mineral insulator include resistance to radiation damage, stability in high temperatures, and noncombustibility. At least the portion of the wires outside of the sensor are covered by a metal jacket such as stainless steel over the mineral insulation.

Probes 17a'–e' and leads 19a'–b' as shown in the arrangement of FIG. 1 are rudundant probes and leads that insure operation of the sensor if any of probes 17a–e or leads 19a–b fail or lose electrical contact with apparatus 10. Additional probes and leads, not shown, can be used to increase the redundancy to ensure a long operating life for the apparatus 10.

Current leads, 19a and 19b, can be formed of any suitable material such as: stainless steel, platinum, nickel, or any other metal or alloy or conductor having suitable properties. The leads can also be covered with a mineral insulation and a metal jacket such as stainless steel.

Preferably, the probe wires ore leads within the sensor are connected by spot welds (not shown) to cable assemblies 31 passing through and sealably attached to end cap 13 by brazes 21. The cable assemblies contain multiple mineral insulated wires covered by a metal, e.g. stainless steel, jacket. Cable assemblies 31 are marketed, for example, by Reutor-Stokes, a division of General Electric Company, Twinsburg, Ohio.

Sensor portion 10A preferably is connected at section 16a to transition member 14 of sleeve portion 10B. This is, transition member 14 is preferably employed to sealably connect sensor portion 10A to sleeve 20 of sleeve portion 10B. Transition member 14 can be the coextruded member or brazed joint described above. Transition member 14 can also be formed from a suitable material which is compatible to both sleeve 20 and sensor portion 10A. This material is then brazed to both section 16a and sleeve 20. Such a material is the Kovar alloy. If a Zircaloy to stainless steel member or joint is used as transition member 14, it is preferred to have Zircaloy to Zircaloy and stainless steel to stainless steel welds. FIG. 1 member 14 is depicted as a Zircaloy to stainless steel member or joint with section 14a' being Zircaloy, section 14a being a Zircaloy to Zircaloy connection, section 14c' being stainless steel, section 14c being a stainless steel to stainless steel connection, and section 14bbeing the point of transition from section 14a' to section 14c'. Other suitable methods of attaching sensor portion 10A to sleeve portion 10B, in addition to brazing to welding can also be employed. End cap 13 is sealably attached, for example by welding, to sleeve 20 and is also preferably of stainless steel. Preferably end cap 13 and sleeve 20 are formed as a single piece. End cap 13 is provided with at least one opening through which cable assemblies 31 pass, the openings and outer sheath of the cable assemblies being sealed by braze 21 to form a moisture-proof seal for channel 10' in apparatus 10. Leads 19a and 19b and probes 17a–e and 17a'–e' are individually connected in electrical contact, for example by spot welding not shown, with the wires in the cable assemblies 31. To minimize potential changes due to thermal gradients within the sensor means, and reduce the pressure differential within and outside the sensor when located in the reactor core, it is preferred that helium or other heat conducting gas be sealed at a suitable pressure that compensates for the high pressure coolant water that will surround the sensor when it is placed in the reactor core.

Corrosion is monitored preferentially be reversing d.c. potential methods. To accomplish this, a reversing direct current is applied to the sensor so as to provide a potential field within the sensor. It is noted that the use of a reversing d.c. potential is not essential to practice this invention. Any means for producing a potential in the sensor is suitable. This can be accomplished by simply applying a current to the sensor. The probe voltage can fall within a wide range, i.e., from about 0.1 microvolts to 12 volts. However, it is desirable to maintain the potential in the microvolt range to avoid excess noise and drift and to minimize electrochemical influences on corrosion of the sensor. These factors will detract from the accuracy of the measurements obtained.

Where it is desirable to maintain the potential in the microvolt range, it may be necessary to amplify the electrical potential measurement obtained across the probes. Amplification as much as 100,000 times or more may be necessary to permit measurements of the electrical potential field within the microvolt range. Where utilizing amplifiers, those which experience low long-term drift, i.e., less than 2 microvolts per year, are preferred. Where such an amplifier is used, the period for current reversal is often limited by the settling time of the amplifier. A one-half second reversal period is adequate for some 1000x gain amplifiers.

The current is preferably reversed periodically to avoid amplifier zero drift and drift due to thermal electromotive forces created at the junction points for the current leads and potential probes. Measurements made with reversed direct current avoids the need for taking a measurement where zero voltage is supplied. By avoiding measurements at zero voltage, inaccuracies due to amplifier zero drift are eliminated. It is preferable to reverse the direct current at a rate within the range of about 0.5 to 4 times per second. Reversing the current at higher rates encourages the problems associated with using alternating current, where the voltage experiences a "skin effect" in which the current density near the surface of the sensor is higher than the subsurface portions of the sensor. Reversing the current at rates lower than 0.5 times per second yields fewer potential readings resulting in lesser resolution of the change in cross-section due to corrosion. The rate at which the current is reversed may be limited by the settling time of the equipment utilized, such as an amplifier. Any conventional switching device is suitable for reversing the direct current. Those devices which experience low drift characteristics, i.e., less than 0.1 percent, and low variances, i.e., less than 0.1 percent, are preferred. The switching device may be controlled by a general purpose computer or other controlling means, such as a timer.

The potential difference across the pairs of first and second probes can be detected by conventional means capable of receiving a voltage across a pair of probes on a conductive material. The probes can be simple contacts, screws, welds and the like where a conductive lead, such as a wire, cable, buss etc. is affixed to the sensor. These conductive leads are affixed to the sensor in a manner which permits electrical conductance to a voltage measuring device, such as a volt meter or an analog/digital converter.

It is preferable to measure the value of the potential difference across the probes continuously; however, intermittent measurements of the potential difference are acceptable and do provide useful information as to the change in cross-section of the sensor from corrosion. It is desirable to measure the potential difference as accurately as possible so as to enhance the determination of corrosion.

To enhance the resolution of the voltage detecting step, an "average measured value" for the potential difference across each pair of first and second probes is obtained by averaging detected values. In general, the more detected values averaged, the higher the resolution.

When utilizing a reversing d.c. potential method, it is preferable to first calculate an average reading per current cycle for each probe pair from at least ten paired detected values (readings), i.e., ten readings are taken when the current is positive and ten readings are taken when the current is negative. These positive and negative readings are preferably detected within milliseconds following the setting time of the amplifier. One-half the difference between the averaged positive and averaged negative readings is calculated and is the average reading per current cycle. In order to increase resolution, it is preferable to average readings for about 100 to 100,000 current cycles to obtain a single reading or the "average measured value". This corresponds to averaging about 1,000 to 1,000,000 paired detected values. By averaging this large number of paired detected values, the signal to noise ratio for the measured values increases. By increasing this ratio, smaller changes in the potential difference across the pairs of first and second probes can be resolved and, therefore, smaller changes in cross-sectional area due to corrosion can similarly be resolved. Depending on the noise in the system, the average measured value obtained from 10,000 paired detected values may give a change in cross section of about 0.1 percent. Systems with more noise will require more detected values for the resolution sought for.

These detected values can be averaged by a general purpose digital computer or by a computer customized to provide the degree of averaging desired. In addition, a circuit which averages the detected potential difference across each pair of first and second probes can be used in lieu of a computer.

A digital computer can calculate the subsequent cross-sectional area values. This data may be communicated to the user by conventional means, such as a visual recorder or by acoustic warning signals. The data may also be communicated to an automatic control mechanism or stored for subsequent analyses and interpretation.

The relationship between current passing through the sensor means and the potential measured is given by the proportional relationship $V \propto IR$ where V is potential measured in voltage, I is current, and R is resistance. While current is fixed by the current throughput through the leads, resistance changes according to radiation damage in the sensor and loss of cross-section due to corrosion of the cylindrical section. Therefore, loss of cross-section due to corrosion can be monitored, for example in scored section 12, by measuring the potentials, $V_1$ and $V_2$, where $V_1$ is the potential measured between the pair of first probes 17c and 17d separated by length $L_1$, and $V_2$ is the potential measured between the pair of second probes 17a and 17b separated by length $L_2$ on the reference section, rod 15, having cross-sectional area $A_2$. Potentials $V_1$ and $V_2$ can be determined by the "average measured value" method described above, and are proportional to the relationships, $$V_1 \propto I\rho \frac{L_1}{A_1},$$

$$V_2 \propto I\rho \frac{L_2}{A_2}$$

where $\rho$ is a constant known to those skilled in the art as the resistivity of the material and depends on factors such as temperature, composition, crystal structure, crystal defects. With I and $\rho$ the same for the reference and cylindrical sections, $$\frac{V_1 A_1}{L_1} \propto \frac{V_2 A_2}{L_2}.$$

The subsequent cross-sectional area, $A_i$, of the cylindrical section between the first pair of probes after corrosion has occurred can be determined according to the proportional relationship:

$$A_i \propto \frac{V_2 A_2 L_1}{V_1 L_2}.$$

If sensor means 10A is comprised of a circular cylindrical section having a mean diameter $D_1$, which is the mean of the inside and outside diameters of the cylindrical section, then the subsequent thickness, $t_i$, of the cylindrical section between the pair of first probes can be determined by the proportional relationship:

$$t_i \propto \frac{V_2 A_2 L_1}{V_1 L_2 \pi D_1}.$$

It should be understood that many pairs of first probes can be located along the cylindrical section to measure potential changes at different sections of the cylindrical section, such as the smooth section and scored section shown in the apparatus above. The appropriate length and potential measurements between the probes are substituted in the above proportional relationships to determine the subsequent cross-sectional area in each of these sections. In addition, multiple pairs of first probes can be placed in electrical contact around the inner surface of the cylindrical section at selected locations, for example, at the beginning and end of the scored section.

In FIG. 1 first probes 17d and 17d, are at one end of the scored section 12, and 17c and 17c' are located at the other end of the scored section forming two pairs of first probes bordering the scored section. A subsequent cross-sectional area that is more representative of the localized region between individual pairs of first probes is determined by measuring the potential between individual pairs of first probes, while an average subsequent cross-sectional area between multiple pairs of probes is determined by measuring an averaged potential between the multiple pairs of probes. For example, first probes 17d and 17d, can be connected in electrical contact and first probes 17c and 17c' can be connected in electrical contact. As a result, an averaged potential is measured between the two pairs of first probes, and an averaged subsequent cross-sectional area in the scored section 12 is calculated therefrom.

Since the measured potential is a function of cross-section, as shown above, a reduced cross-section provides a more sensitive potential measurement that detects smaller changes in cross-section. For example, if the cylindrical section of the sensor described above is reduced from a wall thickness of 30 mils to 10 mils the sensitivity of the potential measurements increases three fold. However, a cylindrical section having such a reduced cross-section may collapse from the pressure of the coolant water surrounding the sensor. Therefore, in another embodiment of the apparatus, a section of the cylindrical section has a reduced wall thickness or cross-section by forming a channel in the circumference of the inside diameter of the cylindrical section. The size of the channel is selected to retain the structural strength in the cylindrical section needed to withstand the pressure from coolant water in a nuclear reactor core. At least one Pair of first probes is placed in electrical contact with the beginning and end of the channel for measuring the potential in the reduced cross-section. The sensor retains the necessary structural strength in the cylindrical section while increased sensitivity of potential measurements is achieved in the reduced cross-section between the channel and the outer surface of the cylindrical section.

Having thus described in detail preferred embodiments of the present invention, it is to be understood that the invention defined by the appended claims is not to be limited by particular details set forth in the above description as many variations thereof are possible without departing form the spirit or scope of the invention.

We claim:

1. An apparatus for monitoring the corrosion of zirconium alloy members in a nuclear reactor core comprising:

a sensor means formed from the zirconium alloy and having a first cylindrical section and a reference section, the first cylindrical section having a first sidewall means extending from a base to form an inner first channel, and the reference section being positioned within the channel and attached to the base so that an electric current can be passed throughout the sensor means;

sleeve means formed from a stainless steel alloy having a second cylindrical section, to second cylindrical section having a second sidewall means extending from a second base to form a second inner channel;

A transition means having coaxial metallurgically bonded third and fourth cylindrical sections so that the third cylindrical section extends from one end and the fourth cylindrical section extends from the other end of the transition means, the third section is formed from the zirconium alloy to mate with the first sidewall means and attached thereto be welding to form a moisture proof seal, the fourth section is formed from the stainless steel alloy to mate with the second sidewall means and attached thereto by welding to form a moisture proof seal;

lead means in electrical contact with the sensor means for passing an electric current through out sensor means, the lead means extending through the first and second channels and through a moistureproof seal in the second base; and probe means in electrical contact with the sensor means for measuring potential in the first cylindrical section and the reference section, the probe means extending through the first and second channels and through a moistureproof seal in the second base.

2. The apparatus of claim 1 wherein the sensor means has the same crystalline texture as the zirconium alloy member.

3. The apparatus of claim 1 wherein the first cylindrical section has an inner surface facing the inner channel and an oppositely facing outer surface, and the outer surface has a scored section and a smooth section.

4. The apparatus of claim 1 wherein the cylindrical section has an inner surface facing the annular channel and an oppositely facing outer surface, and the cross-section of the cylindrical section is reduced by a circumferential channel on the inner surface.

5. The apparatus of claim 3 wherein the probe means are pairs of first probes in electrical contact with the inner surface and at least one pair of second probes in electrical contact with the reference section, and the pairs of first probes bound the scored section and smooth section.

6. The apparatus of claim 4 wherein the probe means are at least one pair of first probes in electrical contact with the inner surface and at least one pair of second probes in electrical contact with the reference section, and the first probes bound the channel.

7. An apparatus for monitoring the corrosion of zirconium alloy members in a nuclear reactor core comprising:
   a generally cylindrical sensor member formed from the zirconium alloy and comprises of sidewall means extending from a first end to a second end, the sidewall means extending to a first access opening at the first end and to a second access opening at the second end and, the sidewall means having an outer surface, and an interior, and a first annular channel extending in the interior from the first end to the second end, and, the outer surface having at least one scored region;
   a first generally circular end cap means of the zirconium alloy sealably attached to the first access opening in relationship therewith so that the first cap retains the first annular channel substantially moisture-free,
   an elongated rod of the zirconium alloy located inside the first annular channel and attached to the first end cap.
   a generally cylindrical sleeve means formed from stainless steel and comprised of sleeve sidewall means extending from a first sleeve end to a second sleeve end, the sleeve sidewall means extending to a first sleeve access opening at the first sleeve end, to a second sleeve access opening at the second sleeve end, and, the sleeve sidewall means having an interior and a second annular channel extending in the interior from the first sleeve end to the second sleeve end.
   a transition member having coaxial metallurgically bonded first and second cylindrical sections defining a third annular channel therein, the first cylindrical section extends from one end of the transition member, and the second cylindrical section extends from the other end of the transition member, the first cylindrical section formed from the zirconium alloy to mate with the second end of the sensor member, and the second cylindrical section formed from the stainless steel to mate with the first sleeve end so that the first, second and third annular channels are contiguous and aligned along the same axis, the first cylindrical section being welded to the sensor member and the second cylindrical section being welded to the first sleeve end to form a moistureproof seal for the channels;
   a first lead in electrical contact with the interior of the sensor member, and a second lead in electrical contact with the rod, the first and second leads insulatively extending from the interior of the sensor member and the rod through the first, second, and third channels,
   at least two probes in electrical contact with the interior of the sensor member and the rod for detecting electrical potential, the probes insulatively extending from the interior of the sensor member and the rod through the first, second, and third channels, and,
   a second end cap sealably attached to the second sleeve end of the sleeve so that the first, second and third channels are retained substantially moisture-free, the second end cap means further comprising means defining at least one opening through which the probes and the first and second leads pass in a moisture-proof seal.

8. The sensor of claim 7 in which the sensor member and rod has the same crystalline texture as the zirconium alloy member.

9. The sensor of claim 7 wherein the probes and the first and second leads are comprised of platinum wire insulated with an outer sheath comprised of ceramic material.

10. The apparatus of claim 7 wherein the outer surface of the sidewall means has a scored section and a smooth section.

* * * * *